(12) United States Patent
Zhang et al.

(10) Patent No.: US 8,877,486 B2
(45) Date of Patent: Nov. 4, 2014

(54) PHOTOBIOREACTOR FOR CARBON DIOXIDE MITIGATION IN WASTEWATER TREATMENT

(75) Inventors: Yalei Zhang, Shanghai (CN); Xuefei Zhou, Shanghai (CN); Hongyang Su, Shanghai (CN); Xiao Chen, Shanghai (CN); Chunmin Zhang, Shanghai (CN); Jinpeng Li, Shanghai (CN)

(73) Assignee: Tongji University, Shanghai (CN)

( * ) Notice: Subject to any disclaimer, the term of this patent is extended or adjusted under 35 U.S.C. 154(b) by 576 days.

(21) Appl. No.: 12/748,813

(22) Filed: Mar. 29, 2010

(65) Prior Publication Data

US 2011/0159581 A1    Jun. 30, 2011

(30) Foreign Application Priority Data

Dec. 30, 2009    (CN) .......................... 2009 1 0247564

(51) Int. Cl.
*C12M 1/00*    (2006.01)
*C12M 1/12*    (2006.01)

(52) U.S. Cl.
CPC ............... *C12M 21/02* (2013.01); *C12M 29/04* (2013.01); *C12M 23/06* (2013.01); *C12M 29/16* (2013.01); *C12M 29/08* (2013.01); *C12M 23/34* (2013.01)

USPC .................. 435/292.1; 435/257.1; 435/295.1; 435/295.2; 435/166; 210/165

(58) Field of Classification Search
USPC ............. 435/292.1, 257.1, 295.1, 295.2, 166; 210/615
See application file for complete search history.

(56) References Cited

U.S. PATENT DOCUMENTS

| 2008/0110828 A1* | 5/2008 | Yerushalmi et al. .......... 210/620 |
| 2008/0160593 A1* | 7/2008 | Oyler ............................ 435/166 |
| 2009/0011492 A1* | 1/2009 | Berzin ........................ 435/257.1 |
| 2009/0197322 A1* | 8/2009 | Goldman .................... 435/257.1 |

OTHER PUBLICATIONS

Chinese Office Action issued in CN2009102475644, dated Jun. 20, 2013.

* cited by examiner

*Primary Examiner* — William H Beisner
*Assistant Examiner* — Danielle Henkel
(74) *Attorney, Agent, or Firm* — Lowe Hauptman & Ham, LLP (57) ABSTRACT

An airlift circulation micro-algae photoautotrophic-heterotrophic coupling photobioreactor for wastewater treatment carbon emission mitigation includes feeding pipe, micro-algae heterotrophic zone, gas-liquid separation chamber, micro-algae phototrophic zone, bottom backflow zone, discharge pipe, and the liquid drained zone.

10 Claims, 7 Drawing Sheets

PHOTOBIOREACTOR FOR CARBON DIOXIDE MITIGATION IN WASTEWATER TREATMENT

RELATED APPLICATIONS

The present application is based on, and claims priority from Chinese Application Number 200910247564.4, filed Dec. 30, 2009, the disclosure of which is hereby incorporated by reference herein in its entirety.

FIELD OF THE INVENTION

This invention belongs to the field of wastewater treatment technology, specifically relates to an airlift circulation microalgae photoautotrophic-heterotrophic coupling photobioreactor for wastewater treatment carbon emission mitigation.

BACKGROUND OF THE INVENTION

Atmospheric carbon dioxide ($CO_2$) concentration being from pre-industrial 270 ppm to the current 380 ppm, $CO_2$ emission mitigation has become the focus of global concern. The government has attached great importance to the issue; all walks of life are working hard to explore the new technologies of $CO_2$ emission mitigation, especially in the wastewater treatment process.

Microalgae and cyanobacteria (blue-green algae) can convert $H_2O$ and $CO_2$ into organic compounds by photosynthesis using photon energy, and has the growth and reproduction capabilities by using mineral nutrients and some organic compounds which are absorbed from the environment. Therefore, it can be used for absorption of wastewater nutrients or biological fixation of $CO_2$ emissions. Its reproductive biomass produced by algae can be used as material for biofuels (for example, bio-diesel, ethanol or methane), animal feed additives, organic fertilizers, etc. Technically, microalgae can be used for many purposes, but the economic feasibility is determinant. Therefore, the cultivation technology, separation technology, and follow-up utilization technologies will greatly affect the utilization and economic viability of microalgae, wherein, high-density cultivation of microalgae by using organic wastewater is a key for wastewater utilization, carbon mitigation for wastewater treatment and low cost microalgae cultivation. And to build photobioreactor (microalgae cultivation reactor) which has a high solar energy utilization rate and high carbon fixation rate suitable for microalgae growth, is the key technology for high-density cultivation of microalgae, wastewater utilization and carbon mitigation for organic wastewater treatment, and has great influence to product quality and production costs of microalgae.

1) Open Photobioreactor

The open photobioreactor is one of the most widely used and mature photobioreactor in microalgae cultivation. It includes two basic types—the horizontal type and oblique type (AE Richmond & Soeder, 1986). Simple structure and low cost are its outstanding advantages. The most typical and commonly used open pond culture system is track pool reactor designed by Oswald (1969), where the mixture and circulation flow of algae liquid are realized by the rotation of the paddle wheel and whirling arm. Now it has enlarged to 180,000 $m^2$ in Taiwan Province of China (*chlorella* production) and 200,000 $m^2$ in Mexico (*Spirulina* production). Since the development of open culture systems, its overall structure is still without a big change. As the open photobioreactor has disadvantages—such as lack of temperature and light control, inadequate mixing, medium susceptible to being contaminated by air-borne micro-organisms and dust. So that there is instability in culture conditions, low photosynthetic efficiency and carbon sequestration efficiency, low overall productivity (the concentration of microalgae in general is 0.1-0.5 g/L or so); and narrow scope of application (only applicable to few microalgae species such as *Spirulina, Chlorella, Dunaliella salina*). The majority of scholars generally believe that the open culture system technology has been developed to the limit, and how to meet the needs of the rapid development of microalgae biotechnology, and to develop a new photobioreactor have become a long-term goal.

2) Closed Photobioreactor

The shortcomings of open channel promote the development of a closed system. The radical solution to the high-density microalgae cultivation is to develop closed photobioreactor, which is a photobioreactor made of transparent tube or container (A Richmond, 1990; Tredici, 2004). In 1950, Cook developed the first vertical tubular photobioreactor. Now, the closed photobioreactor have various types and forms, mainly three types of photobioreactor, namely tubular, plate and traditional tank.

A. Tubular Photobioreactor

Tubular photobioreactor generally uses the transparent hard material (glass or plastic) bent into different shapes with small diameter and connect together, which contains horizontal placed serpentine tubular reactor, double-layer arrangement tubular reactor, multi-branch parallel flow tube reactor, a-type tubular reactor, circular spiral coiled tubular reactor and so on. Tubular photobioreactor is usually with a gas exchange zone, for adding $CO_2$ and nutrients, and removing the oxygen from return flow. The zone is connected with the two pipe ends respectively using the pump or the air-lift device to make the medium circulate in ducts and pipeline (Pirt et al., 1983; A Richmond, Boussiba, Vonshak, & Kopel, 1993).

Most of the existing tubular photobioreactors have the following problems: ① There are difficulties in gas exchange addition of carbon and release of oxygen in the tube cannot be done in time. The dissolved oxygen level of most tubular photobioreactors is more than 200%, so that the photosynthesis and cell growth are greatly inhibited. ② Serious algal cell damage is easily caused because of large shear stress when using mechanical pumps to circulate the algae fluid (Gudin & Chaumont, 1991). Large-scale mixing is even more uneven and mass transfer efficiency is poor. ③ A plug flow state easily forms in the thin and long straight tube, and there are difficulties in forming a good mixing in the cross-section. Due to shading of light by microalgae and limited light path length, microalgae in the reactor cannot receive photon adequately, and the light conversion efficiency of the reactor is low; ④ It is difficult to clean once there is attached-growth of the algae on the internal wall of reactor; ⑤ Investment and maintenance costs are high. The above shortcomings limit its wider application.

B. Flat-plate photobioreactor

Flat-plate photobioreactor has been described by Samson and Leduy (1985 years) for the first time. Now it mainly includes artificial light plate box-type photobioreactor, horizontal flat plate photobioreactor, vertical rabbet plate photobioreactor, multi-layer parallel-plate photobioreactor, oblique bubbling plate photobioreactor etc. Compared with the tubular system, the design of the flat-plate type has the following advantages: ① large light specific surface area, without "dark area", improving the productivity of photosynthesis; ② generally use the ventilation means to promote the mixture and turbulence, low power consumption by air-lift circulation, small damage of shear stress on cells, good mixing, heat transfer and mass transfer efficiency; ③ timely release of oxygen relatively which can be greatly reduced the inhibition of microalgae growth by molecular oxygen; ④ cleaning and maintaining relatively simple. Therefore, the flat-plate reactor as a basic structure has certain advantages.

The structure of plate box type reactor is simple, but it also has some disadvantages, mainly: ① light supply and utilization efficiency. Illumination is one of the most important factors limiting reactor amplification and high-density cultivation of microalgae. When using the external natural light, most patents did not consider how to effectively enhance the algal mixture in the direction of illumination. Coupled with the curtaining of light by surface microalgae, the utilization of light and photosynthesis are limited, which leads to a smaller scale of the reactor. Therefore, there are many patents mainly taking advantage of the internal light source in order to expand the size of the reactor, which increases the operating costs, such as box-type photobioreactor (U.S. patent. US005104803A, Jan. 14, 1992) and internal-light box-type photobioreactor (U.S. Patent. US2003/0059932A1, Mar. 3, 2003). Other scholars (such as Jorg Degen, Li Guang, etc.) add a variety of internal baffle or deflector to achieve enhanced mixing effect of light direction, but it also makes the internal manufacturing and cleaning difficult. Therefore, how to combine the algal concentration, light intensity distribution and mixed-mode to optimize the structure and composition of the reactor in order to enhance solar energy (especially natural light) use efficiency is the core of designing photobioreactor; ② gas supply problems. Because high $CO_2$ concentrations is harmful to microalgae, basically the existing technology use the air to dilute the $CO_2$ to a extent concentration and then send the mixture into the photobioreactor by gas supply device, and simultaneously meet the mixing and mass transfer of $CO_2$ in the algae liquid and lifting the algae liquid. But this also causes difficulties: when the gas supply device adopts small aperture to enhanced $CO_2$ mass transfer, and the mass transfer of oxygen is also enhanced, it allows the power consumption to increase. On the contrary, large aperture devices will limit the absorption and utilization of $CO_2$. Basically, the existing technology in order to dilute the $CO_2$ to a certain concentration in the air after the air supply unit into the light through the bioreactor, and at the same time meet the $CO_2$ in the algae fluid mixing, mass transfer, and enhance the role of algal fluid, As the existing flat-plate reactor is difficult to amplify, the largest volume of the reactor unit is less than 300 L. Large-scale culture systems are realized by increasing the reactor units, which greatly increases manufacturing costs. Excessive reliance on internal sources also significantly increases operating costs. Therefore, the flat-plate reactor, more often at an experimental stage, has not been applied to the industrialization of algae cultivation.

C. Fermenter

Use traditional fermentation tank for microalgae heterotrophic cultivation without restriction of light, rapid growth speed, high yield per unit volume, biomass greatly increased. Using more mature industrial fermentation technology like fed-batch technology is expected to achieve high-density culture, to facilitate reactor amplification and well automated control, but is currently limited to cultivation of a few species of microalgae.

From the foregoing, it is not difficult to find that the existing microalgae cultivation either using photobioreactor for photoautotrophic cultivation with slow growth of microalgae or using fermentation tank for heterotrophic cultivation utilizing organics. Through the appropriate proportion of light-dark area designed and the dispensing of different carbon sources within the photobioreactor, microalgae photoautotrophic process and heterotrophic process can be coupled in one reactor and thus better to play the strong points of photoautotrophic and heterotrophic cultivation, which favors photobioreactor amplification and microalgae cultivation with high-density and low cost, and simultaneously can achieve the goal of organic wastewater utilization and carbon mitigation for wastewater treatment.

SUMMARY OF THE INVENTION

The invention is integrated with characteristics of present photobioreactors and traditional fermenters, the appropriate proportion of light area and dark area, the dispensing of different carbon sources and distribution of molecular oxygen are designed according to microalgae photoautotrophic-heterotrophic carbon sequestration photobioreactor. in terms of optimizing gas ($CO_2$)-liquid mass transfer and increasing microalgae usage efficiency of light energy and carbon source, wastewater treatment carbon emission mitigation air-lift circulation microalgae photoautotrophic-heterotrophic coupling photobioreactor is provided, which has large light specific area, high usage efficiency of light energy, high efficiency of carbon sequestration and better mixing and circulating situation of microalgae culture.

Figure 1:
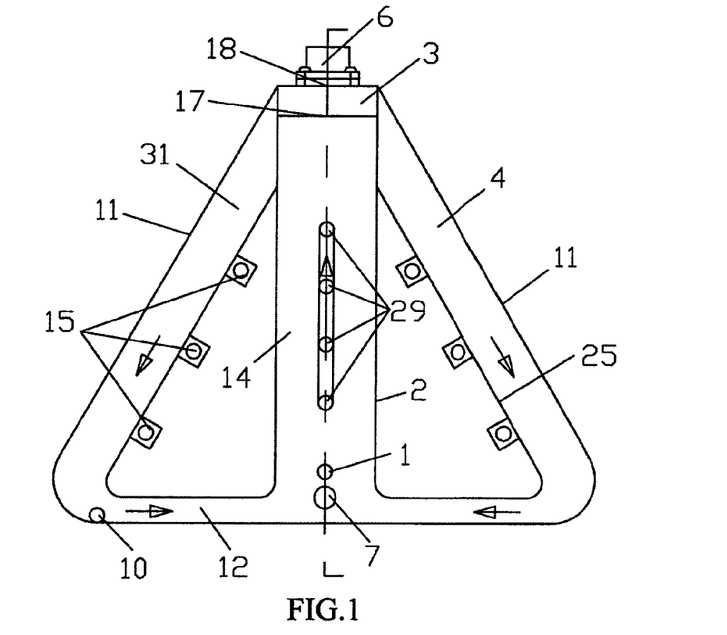
FIG. 1 is a front view of an airlift circulation microalgae photoautotrophic-heterotrophic coupling photobioreactor for wastewater treatment carbon emission mitigation.

The mark numbers in FIG. 1 is feed pipe; 2 is microalgae heterotrophic zone; 3 is gas-liquid separation chamber; 4 is microalgae phototrophic zone; 5 is effluent pipe; 6 is exhaust pipe; 7 is air inlet pipe and flow control valve; 8 is $CO_2$ inlet pipe and flow control valve; 9 is liquid discharging zone; 10 is discharging pipe; 11 is phototaxis plate; 12 is the bottom backflow zone; 13 is air diffusion aerator; 14 is algal liquid lifting zone; 15 is $CO_2$-supply device; 16 is dispensing overflow weir; 17 is effluent overflow weir; 18 is sampling and observation hole; 19 is screws; 20 is seal plate; 21 is frame board for fixation; 22 is stainless steel wire mesh; 23 is flat sheet ultrafiltration membrane; 24 is rectangular hollow box; 25 is backlight board; 26 is the open hole casting end; 27 is the sealing casting end; 28 is hollow fiber membrane; 29 is serpentine heat exchange pipe; 30 is repair and maintenance hole; 31 is photoreaction zone.

DETAILED DESCRIPTION OF THE INVENTION

The invention provides a kind of airlift circulation microalgae photoautotrophic-heterotrophic coupling photobioreactor for wastewater treatment carbon emission reduction. The overall appearance of the reactor is a long ladder consisting of trapezoid in line arrangement, including microalgae heterotrophic zone (2), gas-liquid separation chamber (3), micro-algae photoautotrophic zone (4), bottom backflow zone (12) liquid drained zone (9). therein to:

The microalgae heterotrophic zone (2) is rectangular parallelepiped structure in shape, including feed pipe (1), air diffusion device (13), algae liquid lifting zone (14), and heat exchange pipe (29). The feed pipe (1) is located in middle-lower part of the profile of microalgae heterotrophic zone (2), air diffusion device (13) which connects with air inlet pipe and flow control valve (7) is located at the bottom of microalgae heterotrophic zone (2). Microalgae liquid lifting zone (14) is located in the middle-upper of the microalgae heterotrophic zone (2), the heat exchange pipe (29) is located in the middle of the microalgae liquid lifting zone (14). The microalgae heterotrophic zone (2) connects with gas-liquid separation chamber (3) on the top and bottom connects with recirculation (12) at the bottom.

The gas-liquid separation chamber (3) is symmetric square structure in shape, including the dispensing overflow weir (16), the effluent overflow weir (17), exhaust pipe (6) and the sampling observation hole (18). The dispensing overflow weir 16 is located in the right and left of the gas-liquid separation chamber (3) symmetrically, the effluent overflow weir (17) is located vertically in one side of distributing overflow weir (16) and higher than the dispensing overflow weir (16), the other side of the effluent overflow weir (17) is liquid drained zone (9). The effluent pipe (5) is located at the bottom of liquid drained zone (9) which connects the exhaust pipe (6) on the top, the sampling observation hole (18) is located on the top of the gas-liquid separation chamber (3).

The microalgae autotrophic zone (4) is oblique tetragonal, including the phototaxis board (11), backlight board (25), photoreactions zone (31) and the $CO_2$ gas supply device (15), The phototaxis board (11) is located in the both outer sides of microalgae photoautotrophic zone (4), and angled towards the horizontal plane, the top of which connects with gas-liquid separation chamber (3), the bottom of which connects with bottom backflow area (12), respectively; backlight board (25) is located in the both inner surface of microalgae photoautotrophic zone (4), and the area between light board (11) and backlight board (25) is photoreaction zone (31); $CO_2$ supply device (15) is embedded in the middle part of backlight board (25), and one side of $CO_2$ supply device (15) connects with $CO_2$ inlet pipe and flow control valve (8); dispensing overflow weir (16) is between microalgae photoautotrophic zone (4) and microalgae heterotrophic zone (2).

In this invention, the $CO_2$ gas supply device (15) supply the $CO_2$ gas through flat sheet ultrafiltration membrane, which is cassette structure, according to the thick stainless steel wire mesh (22), flat sheet ultrafiltration membrane (23), thick stainless steel wire mesh (22) and frame board for fixation (21) in turn superimposed are assembled to form membrane module, which is fixed in the hollow rectangular box (24) by screws and bond.

In this invention, the flat sheet ultrafiltration membrane in the $CO_2$ gas supply device (15) can be substituted for the hollow-fiber membrane (28) or tubular microporous aerators. When the gas membrane module were curtain type membrane, the materials of the hollow-fiber membrane (28) can use some known external pressure hollow fiber membrane such as PVDF, polyethylene, polypropylene, polyether siphons, etc. The one casting end of the hollow-fiber membrane (28) is the open hole casting end (26) and the other casting is sealing casting end (27). Casting resin is epoxy resin for sealing and casting, and then carries out secondary casting to the root of hollow fiber membrane (28) using flexible resin such as silicone and Polyurethane. The open hole end connects with $CO_2$ inlet pipe and flow control valve (8).

In this invention, the effective volume ratio of heterotrophic micro-algae zone (2) and photoautotrophic micro-algae zone (4) is from 1:1 to 1:3.

In this invention, the discharging pipe (10) is located at the bottom of the recirculation zone (12) which acts as discharging algae liquid.

In this invention, the liquid discharging zone (9) is the algae liquid discharging zone, which joined gas-liquid separation chamber (3), and algae liquid overflowing from gas-liquid separation chamber (3) is discharged through discharging pipe (5) in liquid discharging zone (9).

In this invention, the air-diffused device (13) is perforated pipe or aerator.

In this invention, the seal plate (20) is set on sampling and observation hole (18), and is fixed on the top of gas-liquid separation chamber (3) by screws.

In this invention, heat-exchanging pipe (9) mentioned above is serpentine heat-exchanging pipe.

Compared with the existing technologies, the advantages of this invention are embodied in the following:

1) According to the characteristics of microalgae photoautotrophic-heterotrophic carbon sequestration reaction, it develops a photobioreactor both suitable for organic wastewater treatment and $CO_2$ sequestration simultaneously, and suitable for wastewater treatment carbon emission mitigation. Microalgae heterotrophic area does not need transparent material. By making use of the characteristics that microalgae heterotrophy does not need light but can utilize organic carbon with high efficiency, it improves microalgae growth, and consume oxygen produced during the photoautotrophic phase and reduce the inhibition effect of dissolved oxygen on photoautotrophic phase. Since there is no light restriction it is favorable for reactor amplification. The photoreaction during photoautotrophic phase can make up for deficiencies of heterotrophic growth, absorb light energy and make use of $CO_2$ with high efficiency.

2) According to the characteristics of gas-liquid mass transfer in the photobioreactor, circumfluence reactor and photoreaction, it innovatively adopts the separation between $CO_2$ supply system and air-lift system, This is totally different from the existing approach of air-lift circulation reactor mixing $CO_2$ and air, namely considering both the supply and mass transfer of $CO_2$ and lift. Its advantages are: ① $CO_2$ and air mixing device is not necessary; ② $CO_2$ can be supplied independently according to $CO_2$ requirement of photoreaction and air stripping may be avoided; ③ flat sheet ultrafiltration membrane (or hollow fiber membrane) is used to supply gas so that $CO_2$ mass transfer and adsorption are strengthened; ④ air only functions in promoting algae liquid flow and stirring, without considering mass transfer, so there is no need using micro-bubble aeration technology, so that resistance loss and power loss can be reduced. It is convenient to change air flow to control the average cycle time and fluid flow velocity of algae liquid in the photobioreactor, strengthening the control over mixing effect and increasing light use efficiency.

3) $CO_2$ is distributed in the photoautotrophic area receiving light, and the direction of distributing parallels that of incident ray, namely, perpendicular to the direction of water flow, Therefore it strengthens algae liquid mixing in the direction of incident ray in the local cross-section, increases light use efficiency and is favorable for amplification of reactor.

4) The reactor adopts the way of inflow at one end and outflow at another end. The cross-section is symmetrical airlift circulation trapezoid structure, and the overall appearance is rectangular parallelepiped, realizing local complete mixing and overall plug flow, so as to ensure mixing and mass transfer effect and increase reaction efficiency.

5) This invention strengthens the release of oxygen, reduces the inhibition effect of molecular oxygen on photoreaction.

6) It increases the light specific area in the photoreaction as much as possible by extending into the air, and makes full use of solar energy. The geometric shape designed can be amplified according to light area requirement and different cross-section shapes can be adopted 7) There are fewer inner components. It is easy to manufacture and simple for operation and maintenance. The cost of manufacturing and operating is low.

8) There is no mechanical device in the photo-bioreactor, eliminating the shear failure effect caused by mechanical agitation on microalgae, greatly enhancing the vitality of microalgae and this is favorable for follow-up solid-liquid separation.

EXAMPLES

Specifically, this invention provides an airlift circulation microalgae photoautotrophic-heterotrophic coupling photo-bioreactor for wastewater treatment carbon emission mitigation, which is applicable to carbon mitigation for the organic wastewater treatment and cultivation of a variety of microalgae with high-density. The structure and operation mode of the invention will be further illustrated with drawings as follows.

Example 1

Figure 2:
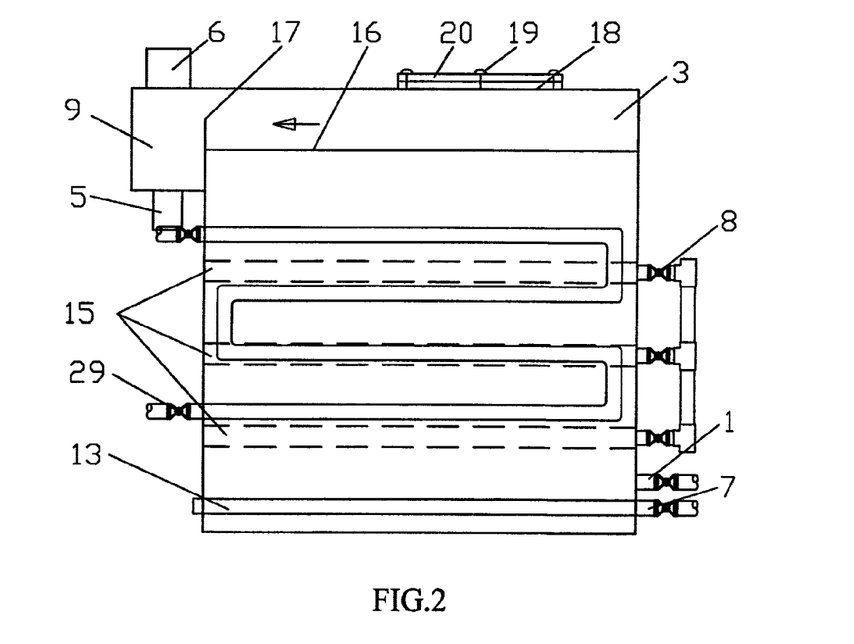
FIG. 2 is a left view of an airlift circulation microalgae photoautotrophic-heterotrophic coupling photobioreactor for wastewater treatment carbon emission mitigation.
Figure 3:
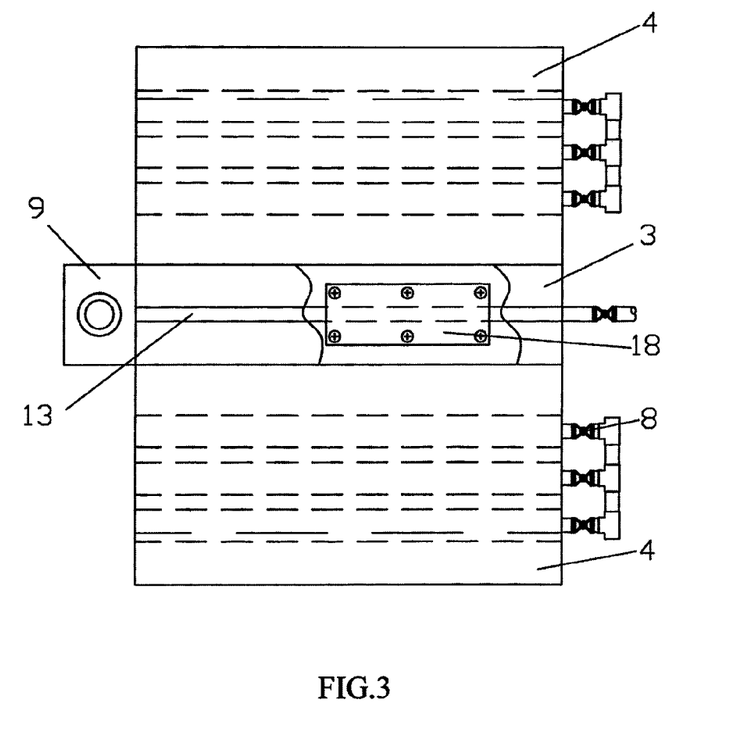
FIG. 3 is a top view of an airlift circulation microalgae photoautotrophic-heterotrophic coupling photobioreactor for wastewater treatment carbon emission mitigation.

Operation Mode 1. Just as FIG. 1-3 show, the overall shape of the airlift circulation microalgae photoautotrophic-heterotrophic coupling photo-bioreactor for wastewater treatment carbon emission mitigation is a long ladder consisting of several trapezoid in line arrangement, including: feed pipe (1), microalgae heterotrophic zone (2), gas-liquid separation chamber (3), microalgae phototrophic zone (4), the bottom backflow zone (12) and liquid discharging zone (9). The arrows in the drawings of the reactor stand for the flow direction of the algal liquid.

Microalgae heterotrophic zone (2) in rectangular parallelepiped shape is the main reaction zone of microalgae heterotrophic growth utilizing the organic matter in the wastewater, which top connects with gas-liquid separation chamber (3) and which bottom connects with the bottom backflow zone (12). It includes feed pipe (1), air inlet pipe and flow control valve (7), air diffusion aerator (13), algal liquid lifting zone (14), and serpentine heat exchange pipe (29) and so on. First, the nutrient solution for cultivating the microalgae (or organic wastewater) flows into middle-lower part of the profile of microalgae heterotrophic zone (2) through feed pipe (1). The microalgae for vaccination flows into the reactor through sampling and observation hole (18) at the top of the reactor, and then mixture, ascending and circulation of algal liquid are promoted by the lifting function of air diffusion aerator (13) located at the bottom of microalgae heterotrophic zone (2). Either perforated pipe or aerator can be used as air diffusion aerator (13), In order to reduce the gas pressure drop, the aeration device should have a large aperture. In order to ensure a better power supply for driving the liquid flow and to ensure a better effect of algal liquid's mixing and lifting, air diffusion aerator (13) should be located at the bottom of the reactor and connected with air inlet pipe and flow control valve (7). The algal liquid lifting zone (14), the shell material of which is opaque material, microalgae, experiences the heterotrophic cultivation without light using organic matter and nutrients in the material (or organic wastewater) from feed pipe (1), The microalgae can achieve a high concentration through heterotrophic processes and consume the DO in the algae fluid, so that the DO concentration and pH value of the algal liquid which flows into the photo-bioreaction zone from the top of it, will decrease. And it also relieves the inhibition of photosynthesis caused by high DO concentration of the algal liquid. Serpentine heat exchange pipe (29) used to control the temperature of algal liquid in the reactor is also located in this zone. Because of the promotion of the air, the algal liquid flows to gas-liquid separation chamber (3) from microalgae heterotrophic zone (2).

In this invention, the gas-liquid separation chamber (3), a symmetrical square structure, respectively connects with microalgae phototrophic zone (4) and with microalgae heterotrophic zone (2), locates on the top of the photo-bioreactor, including the dispensing overflow weir (16), effluent overflow weir (17), the exhaust pipe (6) and sampling and observation hole (18). Among them, algal liquid gets into the gas-liquid separation chamber (3) for gas release, and the released gases are emitted from the top of the exhaust pipe (6) which is sealed by cloth to prevent air pollutants (mainly bacteria, algae and other microorganisms) from contaminating fluid. When the gas is released, algal liquid gets through the dispensing overflow weir symmetrically in the right and left sides, and is evenly distributed to phototrophic microalgae zone (4) on both sides and continues to flow downwards. The effluent overflow weir (17) is higher than the dispensing overflow weir (16) symmetrically on the right and left sides, and perpendicular to them. When there is a continuous influent, the algal liquid overflows into the liquid discharging zone (9) by effluent pipe (5). Sampling and observation hole (18) is also located on the top of the gas-liquid separation chamber (3) for the sampling, observation and microalgae vaccinations.

In this invention, the microalgae photoautotrophic zone (4) is the algal liquid descending zone. It is the tetragonal welded by four plates and is angled towards the horizontal plane. The top of it connects with the gas-liquid separation chamber (3) and the bottom connects with the bottom backflow zone (12). The microalgae photoautotrophic zone (4) contains the phototaxis board (11), backlight board (25), photoreaction zone, the $CO_2$-supply device (15) and repair and maintenance hole (30). The phototaxis board (11) has a certain strength and uses light transparent material such as organic glass or polymer material; The $CO_2$-supply device (15) can use the flat sheet ultrafiltration membrane (23) to supply the $CO_2$, which is embedded in the middle part of backlight board. The gas flow of the $CO_2$ is perpendicular to the liquid flow, namely having reverse direction compared with the incident rays. So, the $CO_2$-supply device (15) not only supplies inorganic carbon source for microalgae growth and regulates the algal solution pH, but also distributes gas evenly, enhances gas-liquid mass transfer and strengthens fluid mixing in the lighting direction, increasing $CO_2$ and solar energy utilization rate. Photoreaction zone is a place where the microalgae converts heterotrophic process into photoautotrophic process which intakes $CO_2$ for photosynthesis, releasing oxygen and simultaneously increasing pH of the algal liquid Then, the algal liquid flows from the bottom backflow zone (12) to the microalgae heterotrophic zone (2) to form the air-lift circulation flow.

Figure 8:
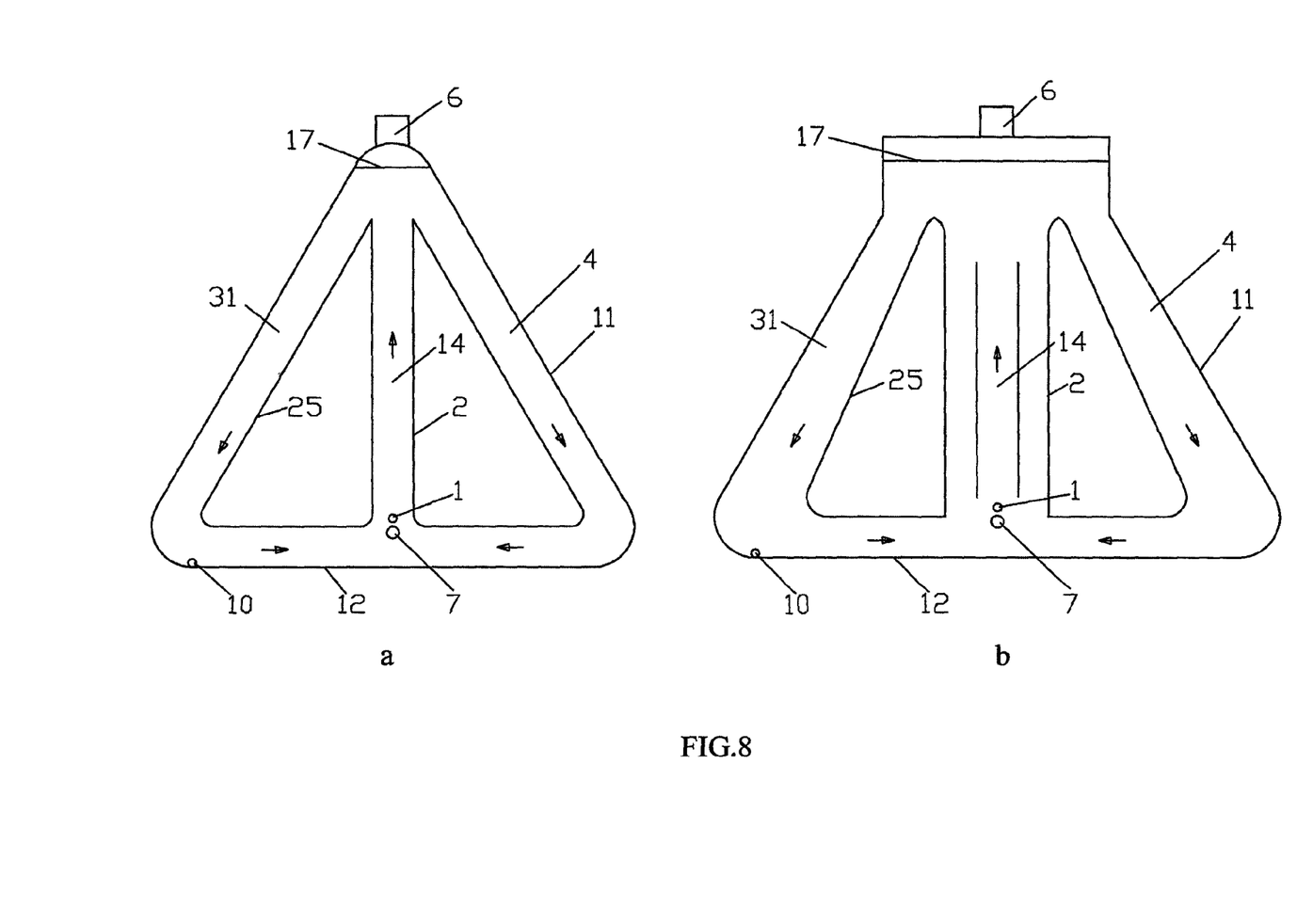
FIG. 8 are several different forms of microalgae photoautotrophic zone and microalgae heterotrophic zone of the airlift circulation microalgae photoautotrophic-heterotrophic coupling photobioreactor for wastewater treatment carbon emission mitigation. Wherein: (a) is the form of internal circumfluence in the microalgae heterotrophic zone, (b) is a triangular form, (c) is a straight square form, (d) is a form. without internal dead space.
Figure 9:
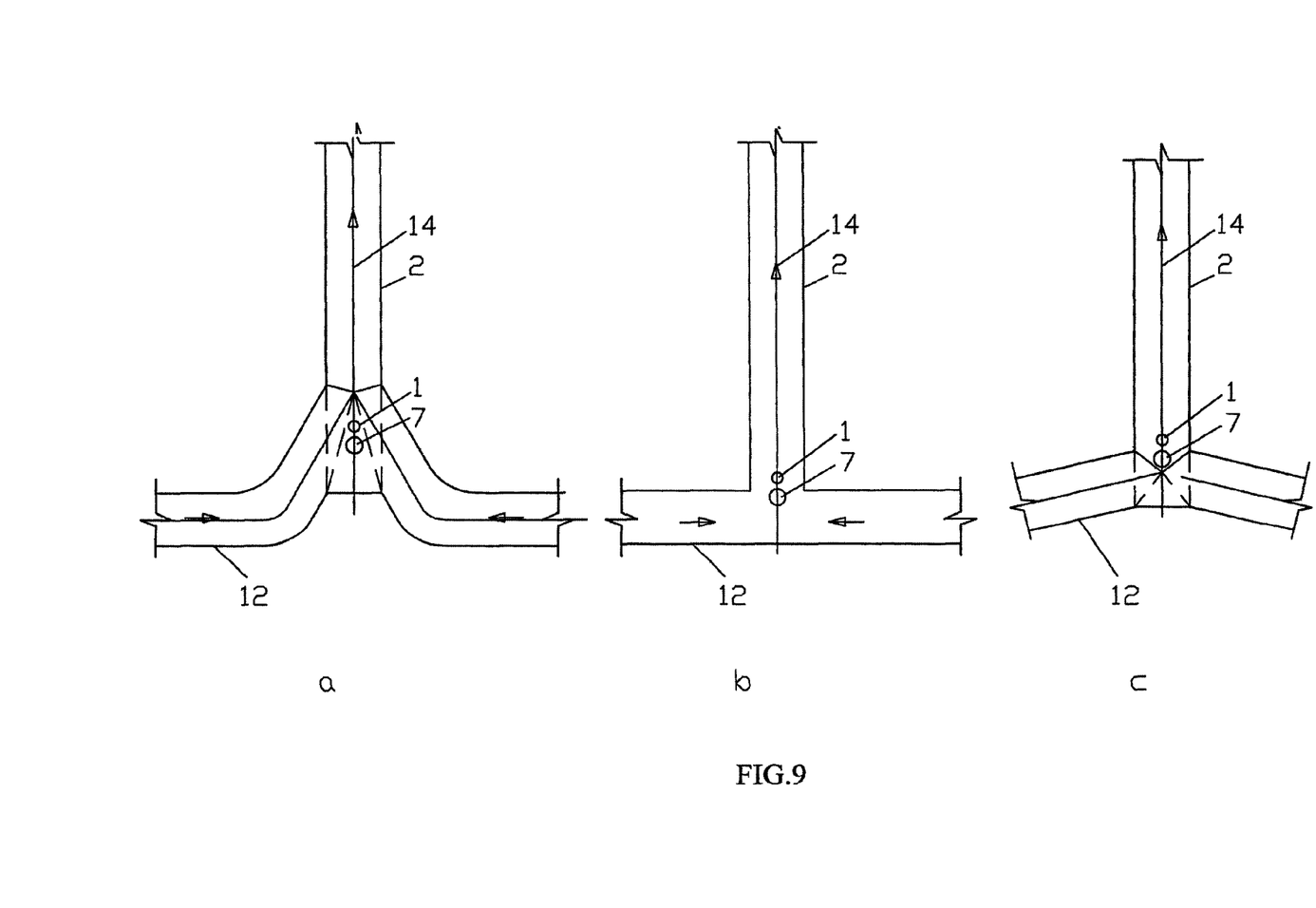
FIG. 9 are several different forms of bottom backflow zone connecting with the heterotrophic zone in the airlift circulation microalgae photoautotrophic-heterotrophic coupling photobioreactor for wastewater treatment carbon emission mitigation. Wherein: (a) is the schema graph of radial pattern connection, (b) is the schema graph of right-angle-type connection, (c) is the schema graph of ramp-type connection.

In a better embodiment, the volume of the microalgae photoautotrophic zone (4) had better be larger than that of the microalgae heterotrophic zone (2). For example, the volume of the microalgae photoautotrophic zone (4) can be 1-3 times the volume of the microalgae heterotrophic zone (2). At the same time, FIG. 8 shows several different patterns of the photoautotrophic zone and the heterotrophic zone of the air-lift circulation photo-bioreactor. FIG. 9 shows several different patterns of the bottom backflow zone connecting with the heterotrophic zone. Among them, the patterns of the photoautotrophic zone and the heterotrophic zone can be trapezoid, triangular, straight square or a form without internal dead space, and the heterotrophic zone also can be internal circumfluence. Several different patterns of the bottom backflow zone connecting with the heterotrophic zone can be radial pattern, right-angle-type connection or ramp-type connection. To sum up, the shape of the airlift circulation microalgae photoautotrophic-heterotrophic coupling photo-bioreactor for wastewater treatment carbon emission mitigation in this invention is not confined to these types mentioned above.

The bottom backflow zone (12) connects with the microalgae photoautotrophic zone (4) and the microalgae heterotrophic zone (2), which makes the photo-bioreactor the circulation reactor, wherein the flow rate of the algal liquid in the photo-bioreactor greater than 0.3 m/s. The ways of the bottom backflow zone (12) connecting with the microalgae heterotrophic zone (2) can be manufactured just as what are showed in FIG. 9.

As shown in FIG. 3, the discharging pipe 10 is installed at the bottom of the bottom backflow zone (12). When it comes to cleaning the reactor or fails in running, the liquid can be discharged here.

Figure 4:
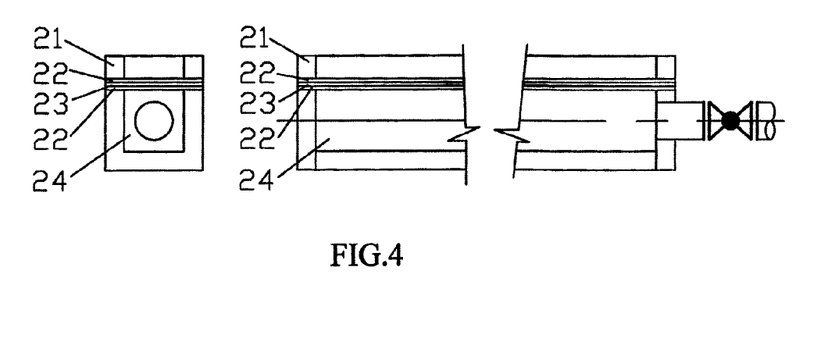
FIG. 4 is a structural diagram of $CO_2$-supply device made of flat sheet ultrafiltration membrane module.

As shown in FIG. 4, the flat sheet ultrafiltration membrane (23) is used in the $CO_2$-supply device 15 in this invention to supply $CO_2$. The $CO_2$-supply device (15) is cassette structure, with thick stainless steel wire mesh (22), flat sheet ultrafiltration membrane (23), thick stainless steel wire mesh (22) and frame board for fixation (21) being assembled in superimposed order to form membrane module, which is fixed in the hollow rectangular box (24) by screws and bond. One side of the $CO_2$-supply device (15) connects with $CO_2$ inlet pipe and flow control valve (8).

Figure 5:
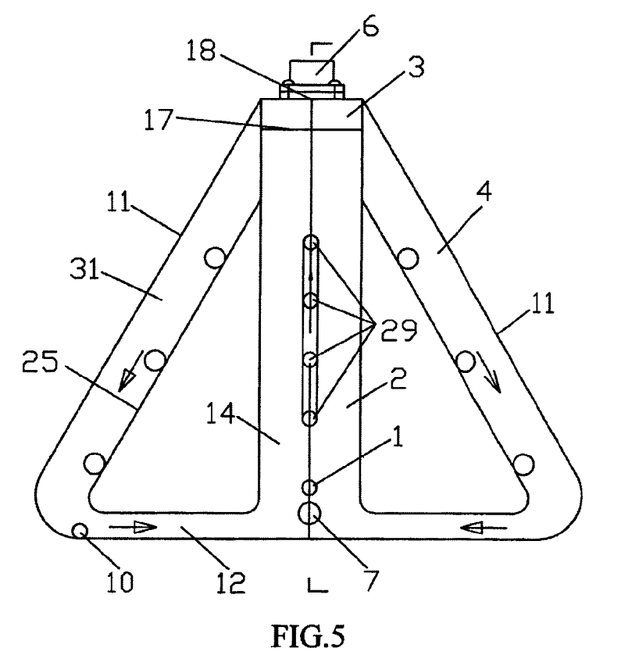
FIG. 5 is a front view of an airlift circulation microalgae photoautotrophic-heterotrophic coupling photobioreactor for wastewater treatment carbon emission mitigation with a built-in curtain-type membrane $CO_2$-supply device.
Figure 6:
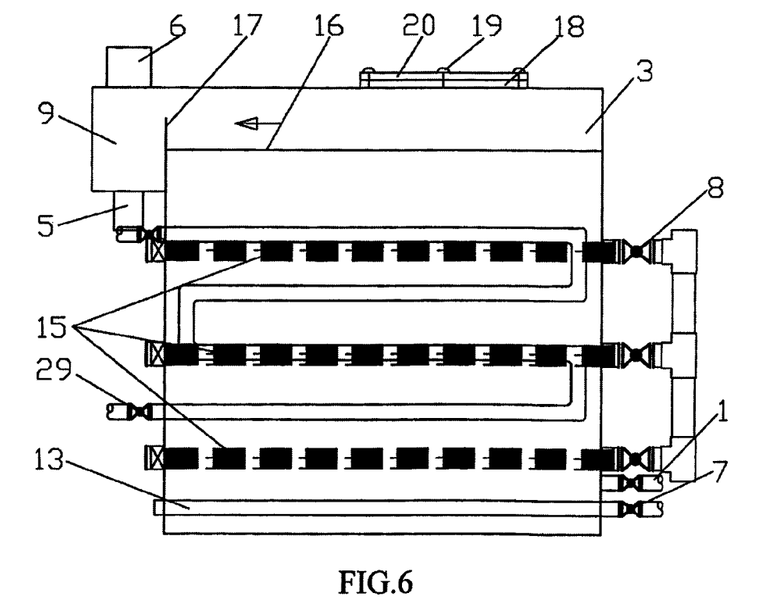
FIG. 6 is a left view of an airlift circulation microalgae photoautotrophic-heterotrophic coupling photobioreactor for wastewater treatment carbon emission mitigation with a built-in curtain-type membrane $CO_2$-supply device.
Figure 7:
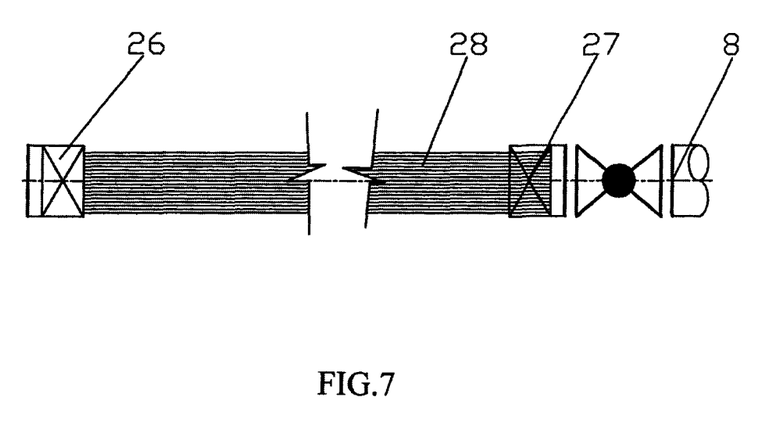
FIG. 7 is a structural diagram of $CO_2$-supply device made of built-in curtain-type membrane module.

As shown in FIG. 5-6, hollow fiber ultrafiltration membrane (28) or tubular microporous aerators can be used as $CO_2$-supply device (15) to replace the flat sheet ultrafiltration membrane. When the gas membrane module is curtain type membrane, the materials of the hollow-fiber membrane (28) can use some known external pressure hollow fiber membrane such as PVDF, polyethylene, polypropylene, polyether siphons, etc. The $CO_2$-supply device (15) with the curtain-type membrane module is shown in FIG. 7. The curtain-type membrane module is closely arranged on the same plane, the number of the wire is 30-60 for the every membrane module. The one casting end of the hollow-fiber membrane (28) is the open hole casting end (26) and the other is sealing casting end (27). Casting resin is epoxy resin for sealing and casting, and then carries out secondary casting in the root of hollow fiber membrane (28) using flexible resin such as silicone and Polyurethane. The open hole end connects with $CO_2$ inlet pipe and flow control valve (8). Casting ends are fixed in the middle part of the boards of the two sides in the microalgae photoautotrophic zone (4). The hollow fiber ultrafiltration membrane (28) is in the microalgae photoautotrophic zone (4), and near the backlight board (25). A certain degree of slack exists between membrane filaments favorable for proper vibration when using to prevent the attached-growth of microalgae.

Effluent pipe (5) can be connected with the separation system, for example, with the flotation tank to concentrate microalgae. And it can also be connected with other systems.

When amplifying the reactor, it has to be reinforced by the steel bracket or other means of stability, in order to prevent deformation of the reactor walls and other issues caused by the increase in reactor's volume and pressure.

The size of the microalgae heterotrophic zone (2) is 300 mm×70 mm×260 mm. The nominal diameter of the feed pipe (1) is 10 mm and is 35 mm away from the bottom, and the nominal diameter of the air inlet pipe (7) is 10-15 mm; Air diffusion equipment (13) is the perforated pipe with the nominal diameter of 15 mm. The length of the pipe is 300 mm, The aperture of holes is 1-5 mm, The pitch of holes is 3-5 mm, and it is 17 mm away from the bottom.

The size of the gas-liquid separation chamber (3) is 300 mm×70 mm×40 mm. The length of the dispensing overflow weir (16) is 300 mm, away from 260 mm at the bottom of the reactor. The length of the effluent overflow weir (17) is 70 mm, and it is 280 mm away from the bottom. The size of the liquid discharging zone is 70 mm×50 mm×70 mm, and the nominal diameter of the discharging pipe is 15 mm.

The size of the phototaxis plate (11) of microalgae photoautotrophic zone (4) is 320 mm×300 mm. And the size of the backlight board (25) is 230 mm×300 mm. The space between them is 65 mm and they have the angle of 60° towards the horizon.

The size of the $CO_2$-supply device (15) is 300 mm×30 mm×30 mm and the size of the flat sheet ultrafiltration membrane (23) is 300 mm×30 mm When the $CO_2$-supply device (15) is made by curtain-type membrane module, the number of the membrane filament is 30-60 for the every membrane module. Then they are fixed on the pipe of DN15. The space between the $CO_2$-supply device (15) is 65 mm.

The thickness of the bottom backflow zone (12) is 18 mm, The size of the bottom board is 314 mm×300 mm. The nominal diameter of the discharge pipe (10) is 10 mm.

The invention claimed is:

1. An airlift circulation microalgae photoautotrophic-heterotrophic coupling photobioreactor for wastewater treatment carbon emission reduction, the overall appearance of the photobioreactor being a long ladder, including a microalgae heterotrophic zone, a gas-liquid separation chamber, a microalgae photoautotrophic zone, a recirculation zone at the bottom of the photobioreactor, and a liquid drained zone;
    wherein the microalgae heterotrophic zone is a rectangular parallelepiped structure, including a feed pipe, an air diffusion device, an algae liquid lifting zone, and a heat exchange pipe; the feed pipe being located in the middle-lower part of the profile of the microalgae heterotrophic zone, the air diffusion device which connects with an air inlet pipe and a flow control valve being located at the bottom of the microalgae heterotrophic zone; the algae liquid lifting zone being located in the middle-upper part of the microalgae heterotrophic zone, the heat exchange pipe being located in the middle of the algae liquid lifting zone; a top of the microalgae heterotrophic zone being configured to connect with the gas-liquid separation chamber; and a bottom of the microalgae zone being configured to connect with the recirculation zone;

wherein the gas-liquid separation chamber is a symmetrical cubic structure, including a dispensing overflow weir, an effluent overflow weir, an exhaust pipe, and a sampling observation hole, the effluent overflow weir being located vertically in one side of the dispensing overflow weir and higher than the dispensing overflow weir, a side of the effluent overflow weir is the liquid drained zone, an effluent pipe being located at the bottom of the liquid drained zone, a top of the liquid drained zone being configured to connect the exhaust pipe, the sampling observation hole being located on the top of the gas-liquid separation chamber;

wherein said microalgae photoautrophic zone is an oblique tetragonal cubic structure, including a phototaxis board, a backlight board, a photoreactions zone, and a $CO_2$ gas supply device; the phototaxis board being located on both outer surfaces of the microalgae photoautotrophic zone, and angled towards a horizontal plane, a top of the phototaxis board being configured to connect with the gas-liquid separation chamber, and a bottom of the phototaxis board being configured to connect with a bottom backflow area; the backlight board being located on the two inner surfaces of the microalgae photoautotrophic zone, and the area between the phototaxis board and backlight board being a photoreaction zone; the $CO_2$ supply device being embedded in the middle part of the backlight board, and one side of the $CO_2$ supply device connects with a $CO_2$ inlet pipe and a flow control valve; the dispensing overflow weir located between the microalgae photoautotrophic zone and the microalgae heterotrophic zone;

wherein the $CO_2$ gas supply device is configured to supply $CO_2$ gas through a flat sheet ultrafiltration membrane, the $CO_2$ gas supply device having a stacked structure, in which a stainless steel wire mesh, the flat sheet ultrafiltration membrane, a stainless steel wire mesh, and a frame board for fixation are assembled in a superimposed order to form a membrane module, which is fixed in a hollow rectangular box, wherein the gas flow of the $CO_2$ is perpendicular to the liquid flow.

2. The photobioreactor of claim 1, wherein the effective volume ratio of the microalgae heterotrophic zone and the microalgae photoautotrophic zone is from 1:1 to 1:3.

3. The photobioreactor of claim 1, wherein the discharging pipe is located at the recirculation zone, which discharging pipe acts to discharge algae liquid.

4. The photobioreactor of claim 1, wherein the liquid drained zone is an algae liquid discharging zone, the liquid drained zone is joined the gas-liquid separation chamber, and algae liquid overflowing from gas-liquid separation chamber is dischargeable through a discharging pipe in the liquid drained zone.

5. The photobioreactor of claim 1, wherein a perforated pipe or an aerator is used as the air diffusion device.

6. The photobioreactor of claim 1, wherein a seal plate is set on the sampling observation hole and is fixed on the top of gas-liquid separation chamber.

7. The photobioreactor of claim 1, wherein said heat-exchanging pipe is a serpentine heat-exchanging tube.

8. An airlift circulation microalgae photoautotrophic-heterotrophic coupling photobioreactor for wastewater treatment carbon emission reduction, the overall appearance of the photobioreactor being a long ladder, including a microalgae heterotrophic zone, a gas-liquid separation chamber, a microalgae photoautotrophic zone, a recirculation zone at the bottom of the photobioreactor, and a liquid drained zone;

wherein the microalgae heterotrophic zone is a rectangular parallelepiped structure, including a feed pipe, an air diffusion device, an algae liquid lifting zone, and a heat exchange pipe; the feed pipe being located in the middle-lower part of the profile of the microalgae heterotrophic zone, the air diffusion device which connects with an air inlet pipe and a flow control valve being located at the bottom of the microalgae heterotrophic zone; the algae liquid lifting zone being located in the middle-upper part of the microalgae heterotrophic zone, the heat exchange pipe being located in the middle of the algae liquid lifting zone; a top of the microalgae heterotrophic zone being configured to connect with the gas-liquid separation chamber; and a bottom of the microalgae zone being configured to connect with the recirculation zone;

wherein the gas-liquid separation chamber is a symmetrical cubic structure, including a dispensing overflow weir, an effluent overflow weir, an exhaust pipe, and a sampling observation hole, the effluent overflow weir being located vertically in one side of the dispensing overflow weir and higher than the dispensing overflow weir, a side of the effluent overflow weir is the liquid drained zone, an effluent pipe being located at the bottom of the liquid drained zone, a top of the liquid drained zone being configured to connect the exhaust pipe, the sampling observation hole being located on the top of the gas-liquid separation chamber;

wherein said microalgae photoautrophic zone is an oblique tetragonal cubic structure, including a phototaxis board, a backlight board, a photoreactions zone, and a $CO_2$ gas supply device; the phototaxis board being located on both outer surfaces of the microalgae photoautotrophic zone, and angled towards a horizontal plane, a top of the phototaxis board being configured to connect with the gas-liquid separation chamber, and a bottom of the phototaxis board being configured to connect with a bottom backflow area; the backlight board being located on the two inner surfaces of the microalgae photoautotrophic zone, and the area between the phototaxis board and backlight board being a photoreaction zone; the $CO_2$ supply device being embedded in the middle part of the backlight board, and one side of the $CO_2$ supply device connects with a $CO_2$ inlet pipe and a flow control valve; the dispensing overflow weir located between the microalgae photoautotrophic zone and the microalgae heterotrophic zone;

wherein the $CO_2$ gas supply device is configured to supply $CO_2$ gas through a hollow-fiber membrane or a tubular microporous aerator, the $CO_2$ gas supply device having a stacked structure, in which a stainless steel wire mesh, the hollow-fiber membrane or the tubular microporous aerator, a stainless steel wire mesh, and a frame board for fixation are assembled in a superimposed order to form a membrane module, which is fixed in a hollow rectangular box, wherein the hollow-fiber membrane comprises at least one selected from the group consisting of PVDF, polyethylene, polypropylene, or polyether siphons, the hollow-fiber membrane having a casting end which is an open hole casting end and another end which is a sealing casting end, the open hole casting end and the sealing casting end including casting resin which is epoxy resin, a root of the hollow fiber membrane having silicone or polyurethane, and the open hole casting end connecting with the $CO_2$ inlet pipe and the flow control valve.

9. The photobioreactor of claim 1, wherein the microalgae heterotrophic zone is the main reaction zone of microalgae heterotrophic growth utilizing the organic matter in the wastewater, and includes the algae liquid lifting zone, the shell material of which is opaque material, microalgae, experiences the heterotrophic cultivation without light using organic matter and nutrients in the material (or organic wastewater) from feed pipe.

10. The photobioreactor of claim 1, wherein the microalgae photoautotrophic zone is the algae liquid descending zone including the phototaxis board which has a certain strength and uses light transparent material such as organic glass or polymer material.

* * * * *